United States Patent [19]

Wateridge et al.

[11] Patent Number: 5,355,891
[45] Date of Patent: Oct. 18, 1994

[54] ECG ANALYZER

[75] Inventors: Steven J. Wateridge; Shaun C. Byrne, both of Oxon, England

[73] Assignee: Oxford Medical Limited, Oxon, United Kingdom

[21] Appl. No.: 3,406

[22] Filed: Jan. 12, 1993

[30] Foreign Application Priority Data

Jan. 13, 1992 [GB] United Kingdom ................ 9200586

[51] Int. Cl.$^5$ ........................................... A61B 5/0452
[52] U.S. Cl. ..................................... 128/702; 128/708
[58] Field of Search ............... 128/696, 700, 702, 703, 128/704, 705, 706, 710, 711, 903, 904, 708

[56] References Cited

U.S. PATENT DOCUMENTS

| | | |
|---|---|---|
| 4,531,527 | 7/1985 | Reinhold, Jr. et al. ............. 128/696 |
| 4,667,682 | 5/1987 | Ihlenfeld, III . |
| 4,947,858 | 8/1990 | Smith . |
| 5,205,295 | 4/1993 | Del Mar et al. ..................... 128/711 |

FOREIGN PATENT DOCUMENTS

0155670A3 9/1985 European Pat. Off. .

OTHER PUBLICATIONS

Tranesjö, et al., "A Versatile System for Exercise ECG Analysis", *IEEE Computers in Cardiology*, pp. 35-38 (Sep. 1985).
Hsia, et al., "An Automated System for ST Segment and Arrhythmia Analysis in Exercise Radionuclide Ventriculography", *IEEE Transactions on Bio-Medical Engineering, BME-33, No. 6*, pp. 585-592 (Jun. 1986).
Akselrod, et al., "Computerized Analysis of ST Segment Changes in Ambulatory Electrocardiograms", *Medical and Biological Engineering and Computing, 25, No. 5*, pp. 513-519 (Sep. 1987).
Jager, et al., "A Real-Time Personal Computer based system for Analysis of Electrocardiograms", *Proceedings Computers in Cardiology*, pp. 497-500 (Sep. 1989).

*Primary Examiner*—Angela D. Sykes
*Assistant Examiner*—George Manuel
*Attorney, Agent, or Firm*—Hoffmann & Baron

[57] ABSTRACT

Apparatus for analyzing ECG signals from a patient in the form of a data stream comprises a data stream monitor to locate for each heart beat a trigger point (26,37,25) having a constant temporal displacement with respect to the location of a portion of the ECG signal (31-34) which may include micropotentials. A processor (15) determines which are acceptable beats and, where a heart beat is acceptable, generates and stores an average from successive portions. The resolution at which the average is stored is such that micropotentials present are detectable. The processor is adapted to store a set of averages generated during a corresponding number of time intervals.

17 Claims, 2 Drawing Sheets

ECG ANALYZER

FIELD OF THE INVENTION

This invention relates to a method and apparatus for analyzing ECG signals from a patient in the form of a data stream.

DESCRIPTION OF THE PRIOR ART

A number of systems exist for analysing ECG signals. Among these are bedside monitors which analyze signals from a patient over a period of time under the control of an operator. Micropotentials are found in ECG's of abnormal patients. For the analysis of micropotentials, a gated average of the heart beat data is stored which requires the rejection of any beats which do not conform to a standard pattern. The patient is required to remain still and quiet whilst being monitored. For micropotentials to be detectable a large amount of high resolution data is stored over a relatively short time period e.g. 15 minutes.

Other systems provide real time analysis storing transient data for real time display, but do not have the facility to store or record high re! solution data obtained over a long period of time.

A number of systems are known for recording electrocardiogram over a defined time period. IEEE Transactions of Biomedical Engineering, Vol. BME-33, No. 6, June 1986, pages 585-592, describes recording data for a patient during an exercise cycle. The data is recorded at 8 bit resolution and stored on tape for subsequent playback as well as providing a real time graphical output. In this system templates are generated from an initial signal and then used for subsequent processing. A disadvantage of this system is that it requires the patient to be connected to equipment which is inconvenient other than for short periods.

Proceedings Computers in Cardiology, Jerusalem, Israel, Sep. 19-22, 1989, IEEE Computer Society Press, Los Alamitos, Calif. pages 497-500, describes a real time personal computer based system for analysis of electrocardiograms for use on hospital wards, during operations or during exercise test analysis. Again the system requires the patient to be connected to equipment which does not allow for longterm monitoring.

IEEE Computers in Cardiology, Sep. 8-11, 1985, Linkoping, Sweden, pages 35-38 describes a simplified software system for analysis of exercise ECGs which is adaptable for use on a number of systems which are concerned with short term monitoring.

It is desirable to obtain data over a longer period e.g. 24 hours, but a system using a bed-side monitor which can be provided with sufficient memory space will be inconvenient to both the patient and the operator and therefore a portable system is desirable.

The measurement of ECG micropotentials on ambulatory patients presents several problems. The two common methods of recording ECG on ambulatory =patients, tape based recorders and solid state recorders]- have limitations when the measurement of micropotentials is required.

Tape based recorders capable of long term recording on an ambulatory patient suffer from inherent distortion in the record/playback process, poor signal to noise ratio, insufficient bandwidth and track misalignment.

Solid state recorders with adequate bandwidth and signal to noise ratio can be produced relatively easily. However, to measure micropotentials it is necessary to sample the ECG at a high rate with good resolution, the currently emerging standard being to sample three channels at a sampling rate of 1 kHz with 12 bit resolution resulting in 4500 bytes per second for each channel which would require 390 Mbyte of memory for 24 hours recording. There is then a problem in storing and processing the large amount of data produced. The memory available and processing power in an ambulatory recorder are limited by cost, size and available battery power. Reducing the amount of data by compression algorithms can distort the signal.

U.S. Pat. No. 4,883,065 describes a conventional Holter system to record long term data on tape. The tape is then played back at high speed and digitized at sufficient resolution and sampling rate to permit analysis of micropotentials. This system suffers from the high noise level and limited bandwidth of tape recording which makes accurate analysis of micropotentials difficult. Also, as micropotential analysis involves forming the vector sum of 3 channels any temporal misalignment, e.g. due to differences in alignment of the replay and recording heads, can cause errors.

SUMMARY OF THE INVENTION

In accordance with the present invention, apparatus for analyzing ECG signals from a patient in the form of a data stream comprises means for monitoring the data stream to locate for each heart beat a trigger point having a constant temporal displacement with respect to the location of a portion of the ECG which may include micropotentials; processing means for determining which are acceptable heart beats and, where a beat is acceptable, for generating and storing an average from successive portions at a resolution such that micropotentials present are detectable, wherein the processing means is adapted to store a set of averages generated during a corresponding number of time intervals.

By storing only relevant portions of the input signal and analyzing the input signal to determine which portions are acceptable and should be used to produce an average and which should be rejected it is possible to obtain accurate readings of micropotentials and permit data to be stored over an extended period without a large memory and power supply requirement. The average produced is permanently stored, if it is acceptable, for accessing at the end of the period for which the ECG signal is analyzed. The averages are uniquely generated for each time interval.

The time lag between a portion of the data stream being defined and analysis of the beat contained within that portion to determine whether or not the portion should be added to the average is limited only by available memory. If there is sufficient memory and processor speed in the device the input data stream may be analyzed at the same resolution as that of the portions of the input data stream, but preferably the monitoring means comprises means to produce a parallel signal from the input data stream at a lower resolution, to monitor the lower resolution data stream to determine the approximate position of a trigger point, and thereafter to monitor the higher resolution data to determine trigger point location.

The apparatus described may be used to monitor patients at the bed-side, but preferably the apparatus is suitable for ambulatory use, and can be carried by the patient in a manner similar to Holter or other ambulatory equipment.

Preferably the apparatus further comprises means to set a fixed time interval for generating and storing am average from successive portions.

Preferably the apparatus further comprises means to set a monitoring period. Preferably display means display averages for a number of fixed time intervals within e monitoring period sequentially. This enables the changing shape of a heart beat to be monitored over a monitoring period. Trends of data parameters may be obtained from the data within each average over the monitoring period.

In accordance with a second aspect of the present invention, a method of analyzing an ECG signal from a patient in the form of a data stream comprises monitoring the data stream to locate for each heart beat a trigger point having a constant temporal displacement with respect to the location of a portion of the ECG which may include micropotentials; determining which are acceptable hear beats and for an acceptable heart beat, generating an storing an average from successive portions at a resolution such that micropotentials present are detectable; an storing a set of averages generated during a corresponding number of time intervals.

Preferably the time intervals are spaced apart. Generation and storage of an average from successive portions may take place over any time interval within the limitations of the memory and power supply available, but preferably, it takes place over a fixed time interval. This allows waveforms to be produced which can be compared with one another directly. It also allows changes which occur during the monitoring period to be observed.

Typically the fixed time interval is between 5 and 15 minutes. The patient may be monitored for one fixed time interval, to produce one waveform or for several hours, but preferably the patient is monitored for a period of 24 hours.

The method of analysing an ECG signal may be carried out at only one resolution but preferably further comprises producing a parallel signal from the input data stream at a lower resolution; monitoring the lower resolution data stream to determine the approximate position of a trigger point, and thereafter monitoring the higher resolution data to determine trigger point location.

Acceptability of a heart beat is typically determined by comparison of a waveform representing the beat with one or more templates. The comparison may be with templates at the same resolution at which acceptable portions will be stored but preferably comparison is between the parallel signal at the lower resolution and one or more templates at the lower resolution. Once a waveform has been determined to be acceptable it can be used to generate an average for the time interval. This average is stored without further reference to the stored templates. It provides a more accurate representation of the high resolution signals recorded than prior art systems.

BRIEF DESCRIPTION OF THE DRAWINGS

An example of a method and apparatus for analyzing ECG signals in accordance with the present invention will now be described with reference to the accompanying drawings, in which.

EMBODIMENT

Figure 3:
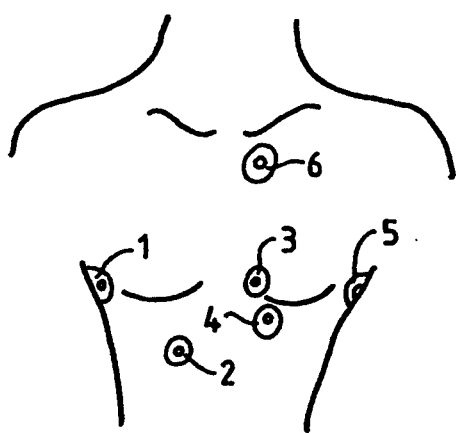

Three channels of data in X, Y, and Z directions respectively are obtained by positioning electrode leads as shown in FIG. 3. The X channel positive and negative electrodes are positioned at points 5 and 1, the Y channel electrodes at points 4 and 6, and the Z channel electrodes at point 3 and an equivalent position on the back of the patient. A ground connection is provided at position 2. Each channel of data is processed separately.

Figure 1:
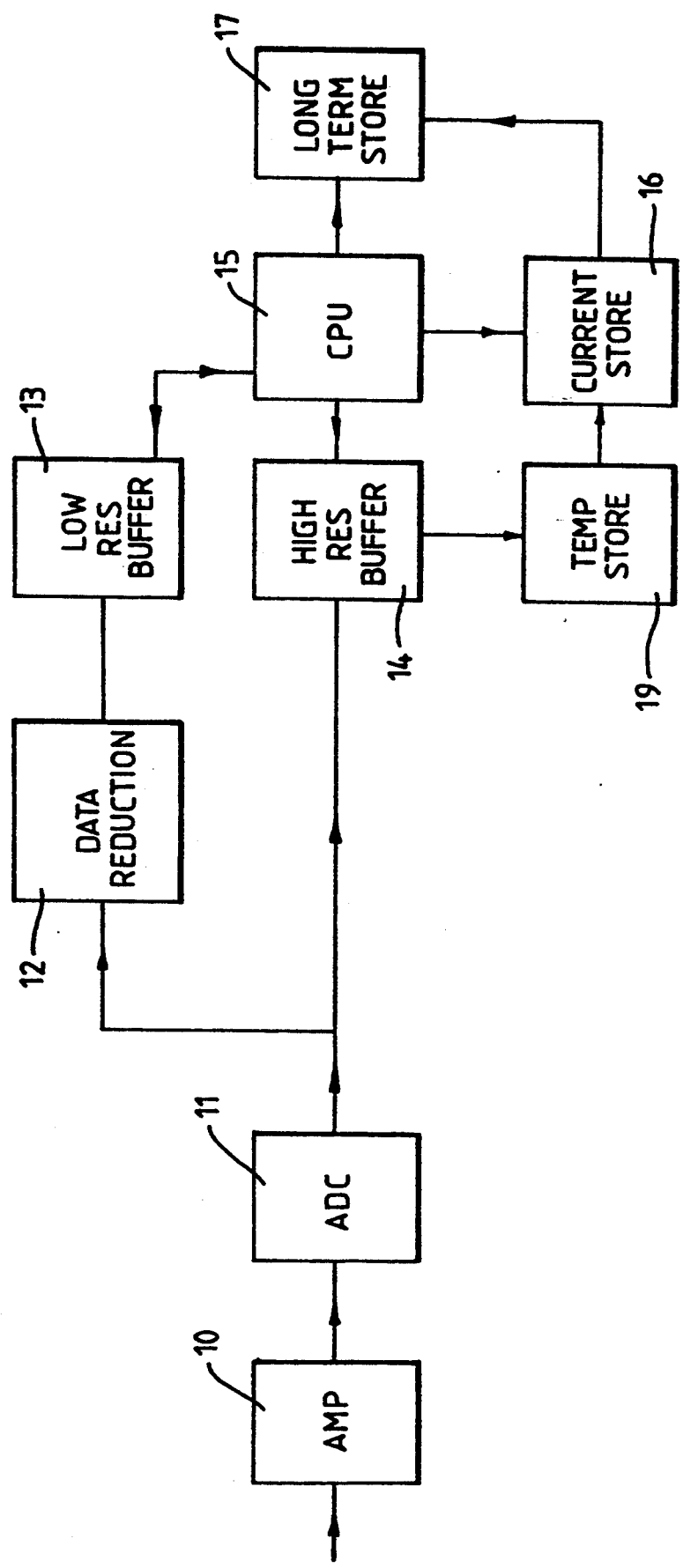
FIG. 1 is a block diagram of apparatus according to the invention.

FIG. 1 shows a block diagram of apparatus incorporating one example of the present invention. A single channel of data from the patient is input to an amplifier 10 and after amplification converted from an analogue signal to a digital signal by an analogue to digital converter (ADC) 11 at a high resolution and sampling rate, e.g. 500 Hz/12 bits. Output from the ADC passes in parallel directly to a high resolution buffer 14 and via a data reduction circuit 12, which averages groups of samples from the high resolution data to produce a low resolution data stream, to a low resolution buffer 13. Data in the low resolution buffer 13 is then examined by a microcomputer (CPU) 15 using a trigger algorithm.

Figure 2:
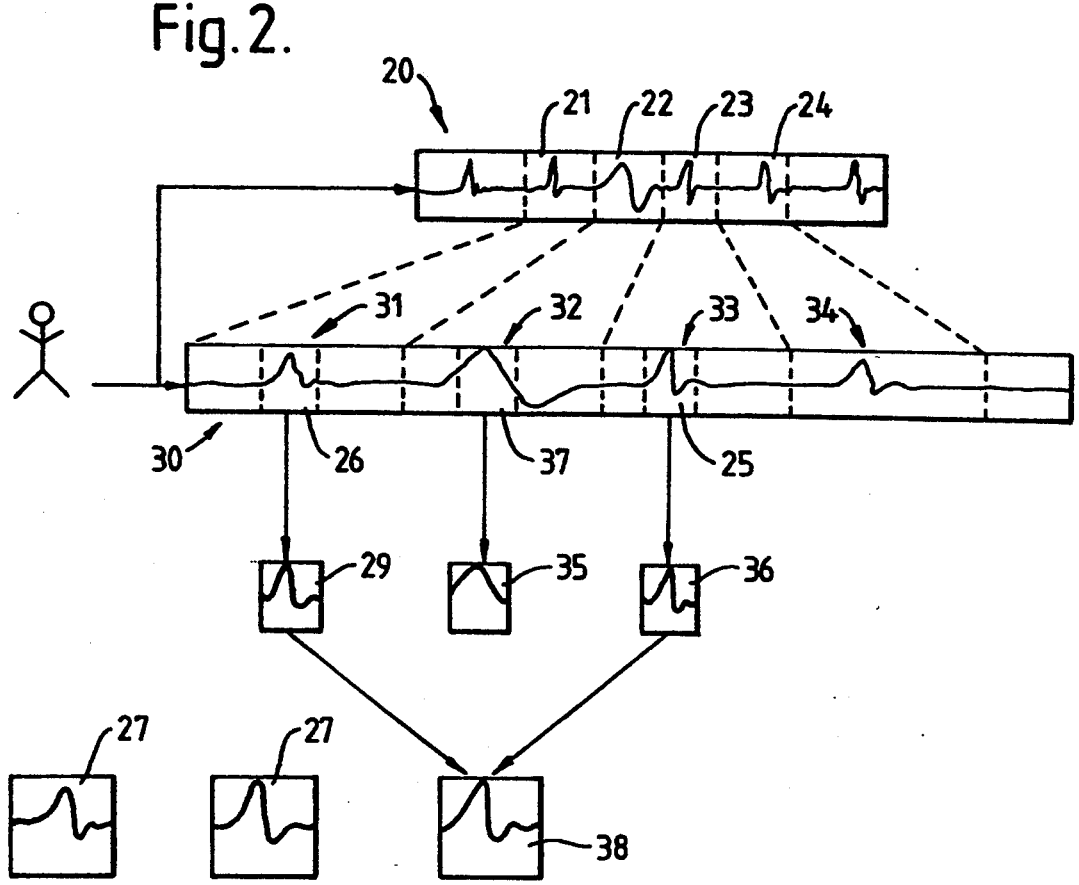
FIG. 2 illustrates typical data input for parallel high and low resolution versions of the input data stream; and, FIG. 3 illustrates typical electrode placement on a patient's body to take ECG measurements.

An example of a set of low resolution data 20 stored in the buffer 13 is illustrated in FIG. 2. The trigger algorithm scans the data 20 to detect the occurrence of heart beats 21 to 24 and produces a trigger point for each beat detected. The trigger point may be a positive or negative peak of the signal, zero crossing or position of maximum slope, or preferably the mid point between minimum and maximum slopes. For each trigger point the corresponding region 31–34 of the high resolution data buffer 14 is examined to accurately determine a position of the beat. Thus the high resolution data need only be analyzed in the region of a known trigger point 26, 37, 25 thereby reducing the time required to accurately determine the trigger point from the high resolution data. Using a low resolution data stream for analysis of the trigger point allows a low power microprocessor to be used.

A short sequence of data around each trigger point 26, 37, 25 is then copied from the high resolution data buffer 14 under control of a CPU 15 to a temporary store 19 which can be embodied in a FIFO. The corresponding data in the high resolution buffer 14 is then discarded. By continuously carrying out this process a series of short portions of high resolution data 29,35,36 are produced representing each beat on each channel.

The low resolution data buffer 13 is analyzed to determine which beats should be used for the measurement of micropotentials. This enables noisy and ectopic beats to be rejected. The analysis may make use of a series of templates, in this example 40 templates although other numbers may be used, to which the sample is matched. The templates are generated from patient data during analysis. For each qualified or acceptable beat the corresponding high resolution data, in this example, portions 29,36 in the temporary store 19 is used to generate an average in a current store 16 by summing the data for each beat over a fixed time period and dividing by the number of beats stored. At the beginning of the fixed time period no data is present in the current store 16 and the waveform of the first portion deemed to be acceptable will be stored directly.

Alternatively, averages of a fixed number of beats may be taken or averaging continued until a particular signal to noise ratio is achieved.

For a beat 35 which does not qualify as a good beat, the corresponding high resolution data is discarded. When data has been transferred from the temporary store 19 to the current store 16 it is then discarded from the temporary store. After a predetermined time period, typically between 5 and 15 minutes the data in the current store 16 is transferred to a long term store 17 and the current store begins to store new data. The long term store 17 stores a series of sequentially addressable data 27 each of which is a waveform of the average of all the acceptable portions input to the current store in each fixed time period. The current store contains a gated average of all the acceptable data stored over the predefined time period.

The gated averages 27 are free of distortion caused by recording the ECG signals onto tape or using compression algorithms to store the data in solid state memory. The series of representations enables trends of parameters, for example, beat width or micropotential amplitude to be produced for the whole of the recording period when the data in the store 17 is replayed, for example displayed on a monitor. The number of beats used to produce each representation is also recorded. When replayed, weighted averages of 2 or more representations may be produced to obtain the required compromise between temporal resolution and signal to noise ratio. The three channels X, Y, and Z can be combined to produce a vector signal for display using the root mean square (rms) of the signal in each channel.

No operator intervention is required to produce a record of micropotentials over an extended period e.g. 24 hours, by using the method and apparatus of the present invention.

We claim:

1. Apparatus for analyzing ECG signals from a patient in the form of a data stream, the apparatus comprising means for monitoring the data stream to detect the occurrence of heart beats and generate a trigger point for each beat detected, the trigger point defining a region of data which is examined by the monitoring means to accurately determine a location of a portion of said ECG signal which may include micropotentials; processing means for determining which are acceptable heart beats and, where a heart beat is acceptable, for generating and storing an average from successive portions of said ECG signal at a resolution to detect micropotentials, wherein said processing means is adapted to store a set of averaged data generated during a corresponding number of time intervals.

2. Apparatus according to claim 1, said monitoring means comprising means to produce a parallel signal from said data stream at a low resolution, to monitor said low resolution data stream to determine the approximate position of said trigger point, and thereafter to monitor said data stream at a high resolution to determine a trigger point location.

3. Apparatus according to claim 1 which is suitable for ambulatory use.

4. Apparatus according to claim 1 further comprising means to set a fixed time interval for generating and storing said averaged data from successive time intervals.

5. Apparatus according to claim 1 further comprising means to set a monitoring period.

6. Display means to display averages produced by apparatus according to claim 1, said display means displaying averages for a number of fixed time intervals within a monitoring period sequentially.

7. A method of analyzing an ECG signal from a patient in the form of a data stream, the method comprising monitoring said data stream to to detect the occurrence of heart beats and generate a trigger point for each beat detected, the trigger point defining a region of data, and examining the region of data to accurately determine a location of a portion of said ECG signal which may include micropotentials; determining which are acceptable heart beats and for an acceptable heart beat, generating and storing an average from successive portions at a resolution to detect micropotentials; and storing a set of averages generated during a corresponding number of time intervals.

8. A method according to claim 7, wherein said time intervals are spaced apart.

9. A method according to claim 7, wherein generation and storage of an average from successive portions takes place over a fixed time interval.

10. A method according to claim 9 wherein said fixed time interval is between 5 and 15 minutes.

11. A method according to claim 7, wherein the patient is monitored for a period of 24 hours.

12. A method according to claim 7 further comprising producing a parallel signal from said data stream at a low resolution; monitoring the low resolution data stream to determine the approximate position of a trigger point, and thereafter monitoring the said data stream at a higher resolution to determine trigger point location.

13. A method according to claim 7, wherein acceptability of a heart beat is determined by comparison of a waveform representing said heart beat with one or more templates.

14. A method according to claim 12, wherein acceptability of a heart beat is determined by comparison of said parallel signal from said data stream at said low resolution and one or more templates at said low resolution.

15. Apparatus for analyzing ECG signals from a patient in the form of a data stream, the apparatus comprising means for monitoring the data stream to locate for each heart beat a trigger point having a constant temporal displacement with respect to a location of a portion of said ECG signal which may include micropotentials; processing means for determining which are acceptable heart beats and, where a heart beat is acceptable, for generating and storing an average from successive portions at a resolution to detect micropotentials, wherein said processing means is adapted to store a set of averages generated during a corresponding number of time intervals, and wherein said monitoring means comprises means to produce a parallel signal from said data stream at a low resolution, to monitor said lower resolution data stream to determine the approximate position of said trigger point, and thereafter to monitor at a high resolution said data stream to determine a trigger point location.

16. A method of analyzing an ECG signal from a patient in the form of a data stream, the method comprising monitoring said data stream to locate for each beat a trigger point having a constant temporal displacement with respect to a location of a portion of said ECG signal which may include micropotentials; producing a parallel signal from said data stream at a low resolution; monitoring the lower resolution data stream to determine the approximate position of a trigger point, and thereafter monitoring at a high resolution said data stream to determine trigger point location; determining which are acceptable heart beats and for an acceptable heart beat, generating and storing an average from successive portions at a resolution. To detect micropotentials; and storing a set of averages generated during a corresponding number of time intervals.

17. A method according to claim 16, wherein acceptability of a heart beat is determined by comparison of said parallel signal from said data stream at said lower resolution and one or more templates at said lower resolution.

* * * * *